Sept. 28, 1954 E. S. BOERNER Plant Pat. 1,305
CHRYSANTHEMUM PLANT
Filed Oct. 6, 1953
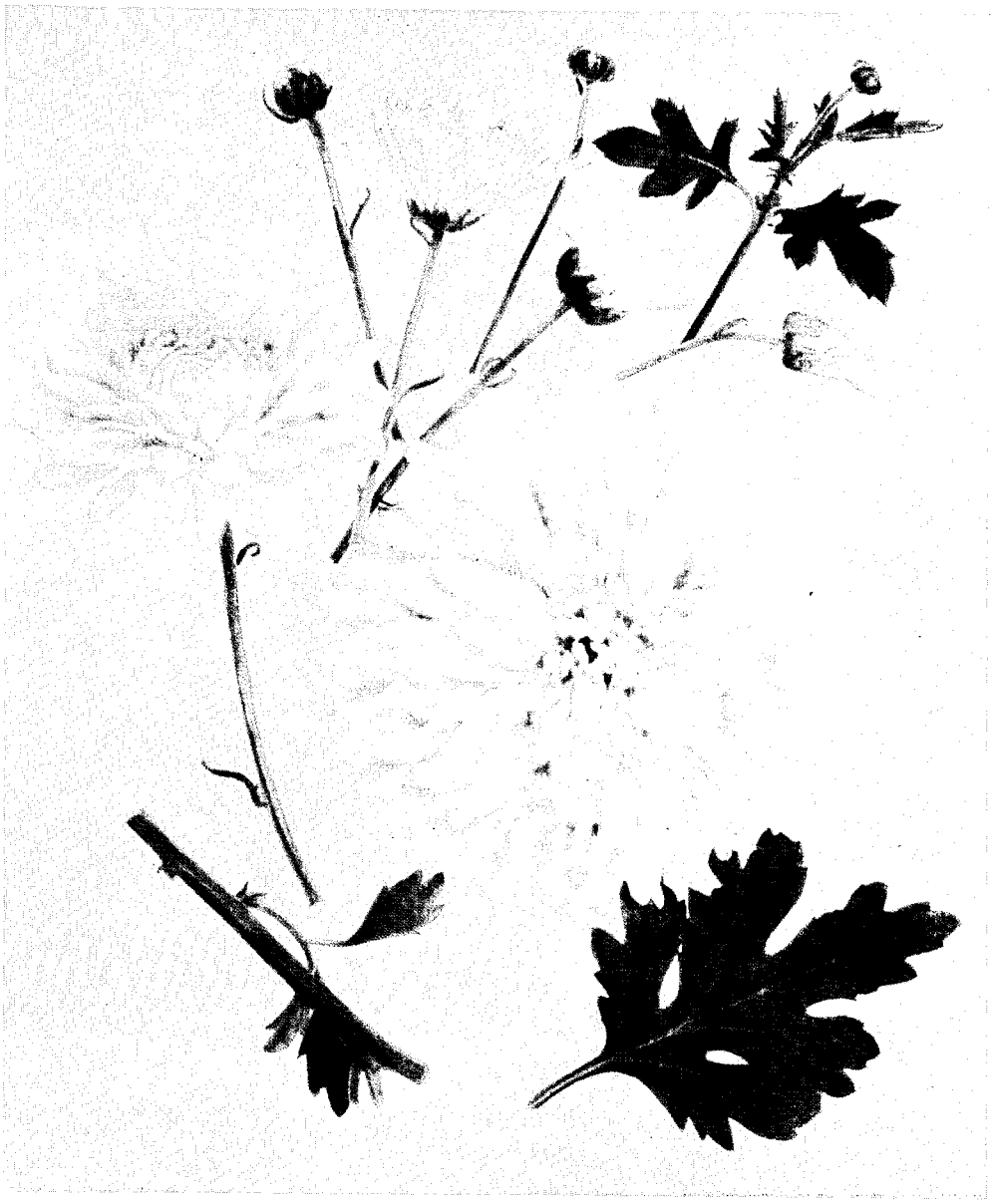
Inventor.
E. S. Boerner
By: Robb & Robb
Attorneys Patented Sept. 28, 1954

Plant Pat. 1,305

UNITED STATES PATENT OFFICE 1,305

CHRYSANTHEMUM PLANT

Eugene S. Boerner, Newark, N. Y., assignor to Jackson & Perkins Company, Newark, N. Y., a corporation of New York Application October 6, 1953, Serial No. 384,534

1 Claim. (Cl. 47—60)

The present invention relates to a new and distinct variety of chrysanthemum plant of the semi-decorative type, which was originated by me by crossing the variety "Lavender Lady" (unpatented) with the variety "Mrs. Du Pont" (unpatented).

The primary objective of this breeding was to produce a new variety of chrysanthemum having flowers of a size and quantity comparable to the variety "Lavender Lady," but the flowers of which are of a color comparable to those of the variety "Mrs. Du Pont." This objective was fully achieved, as evidenced by the fact that my new variety bears larger and fuller flowers similar to "Lavender Lady," while in the color of "Mrs. Du Pont." This unique combination of characteristics, together with the unusual freedom of reproduction of my new variety by suckers, distinguish the new variety from its parents, as well as from all other varieties of its class, and asexual reproduction of the new variety by top cuttings and also by underground runners, at Newark, New York, shows that the foregoing characteristics and distinctions come true to form and are established and transmitted through succeeding propagations.

The accompanying drawing shows typical specimens of my new variety, with the flowers, foliage and stems in different stages of development, and as depicted in color as nearly true as it is reasonably possible to make the same in a color illustration of this character.

The following is a detailed description of my new variety, as grown and observed in fields at Newark, New York, in the early part of the month of October and in the midmorning, with color terminology in accordance with Ridgway's Color Standards and Nomenclature:

Parentage: "Lavender Lady" × Mrs. Du Pont."
Classification: Semi-decorative.
Growth: Vigorous; upright; strong; attains a height of 30 inches.
Cold resistance: Plants are winter hardy in northern New York; flowers show little frost burn with early frosts.

Blooming period: In Newark, New York climatic area, average date of start of blooms is about September 25th, and blooming continues until heavy freezes in October.

Bud:
- *Color.*—When sepals first divide—Capucine Buff, Plate 3. When petals begin to unfurl—Pale Orange-Yellow, Plate 3. When half blown—inside of petals—Capucine Orange, Plate 3. Reverse of petals—Buff Yellow, Plate 4.
- *Peduncle.*—Color—Light Cress Green, Plate 31. Strength—strong.

Bloom:
- *Size.*—3½ to 4 inches.
- *Stem.*—Strong; normal.
- *Form.*—Semi-decorative.
- *Petalage.*—Full double.
- *Color.*—Center of flower—Salmon Orange, Plate 2. Outer petals—Capucine Yellow, Plate 3. Base of petals—Light Green Yellow, Plate 5. Inside of petals—Capucine Yellow, Plate 3, lightly overcast with Salmon Orange, Plate 2. Reverse of petals—Buff Yellow, Plate 4.
- *Petals.*—Texture—medium stiff. Form—oval.

Fragrance: Characteristic chrysanthemum.

Plant:
- *Form.*—Upright; compact.
- *Growth.*—Free.

Foliage:
- *Size.*—Large.
- *Quantity.*—Normal.
- *Color.*—Upper side—Forest Green, Plate 17. Reverse side—Light Bice Green, Plate 17.
- *Texture.*—Leathery.

I claim:

A new and distinct variety of chrysanthemum plant of the semi-decorative type, substantially as herein shown and described, characterized particularly as to novelty by its upright growth and great floriferousness, by the relative large size, fullness and distinctive color of its flowers, and by its freedom of reproduction by suckers.

No references cited.